United States Patent [19]

Welstead, Jr.

[11] Patent Number: 4,605,652
[45] Date of Patent: Aug. 12, 1986

[54] METHOD OF ENHANCING MEMORY OR CORRECTING MEMORY DEFICIENCY WITH ARYLAMIDO (AND ARYLTHIOAMIDO)-AZABICYCLOALKANES

[75] Inventor: William J. Welstead, Jr., Richmond, Va.

[73] Assignee: A. H. Robins Company, Inc., Richmond, Va.

[21] Appl. No.: 697,944

[22] Filed: Feb. 4, 1985

[51] Int. Cl.$^4$ .......................................... A61K 31/55
[52] U.S. Cl. ................................................. 514/214
[58] Field of Search ....................................... 514/214

[56] References Cited

U.S. PATENT DOCUMENTS 4,213,983  7/1980  Hadley et al. .................. 260/239 B

FOREIGN PATENT DOCUMENTS 0099789  2/1984  European Pat. Off.
2531083  2/1984  France.
1293446  10/1972  United Kingdom.
2125398  3/1984  United Kingdom.

Primary Examiner—Stanley J. Friedman

[57] ABSTRACT

A pharmaceutical method for improving memory or correcting memory deficiency is disclosed, utilizing compounds having the formula:

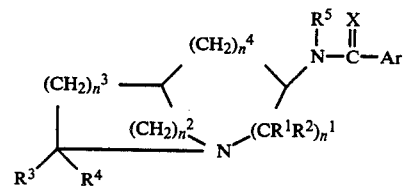

wherein $n^1$, $n^2$, $n^3$, and $n^4 = 0$ to 3; $R^1$, $R^2$, $R^3$, and $R^4 = H$, loweralkyl or phenyl; $R^5 = H$ or loweralkyl; $X = O$ or $S$; $Ar =$ phenyl, substituted phenyl, pyridinyl, furanyl, thienyl, methoxy-1H-benzotriazolyl, indolinyl, methoxyindolinyl, methoxypyrimidinyl, amino-methoxypyrimadinyl, 1,3-benzodioxolyl, or naphthalenyl, and the pharmaceutically acceptable acid addition salts, hydrates and alcoholates thereof.

19 Claims, No Drawings

METHOD OF ENHANCING MEMORY OR CORRECTING MEMORY DEFICIENCY WITH ARYLAMIDO (AND ARYLTHIOAMIDO)-AZABICYCLOALKANES

BACKGROUND OF THE INVENTION

1. Field of Invention

This invention relates to a method of improving the memory of living animals with certain arylamidoazabicycloalkanes. The invention contemplates the treatment of memory deficiencies and disorders associated with Alzheimers disease and other forms of sinility.

2. Information Disclosure Statement

Various chemicals such as physostigmine, arecholine, choline or piracetam have been reported to facilitate memory in animals, KIRK OTHMER, ENCYCL. CHEM. TECHNOL., 3rd Ed. (1981) Vol. 15, pp 132-142 and ANNUAL REPORTS IN MEDICINAL CHEMISTRY (1984) Vol. 19, pp 31-43. The cardiovascular drug procainamide has been tested for learning enhancement activity in experimental animals of different ages and has been said to improve learning deficits in aging rats KIRK OTHMER ibid p. 139. Ergoloid Mesylates have been used in treatment of impaired mental function in the elderly. The ergoloid mesylates may in some cases give rise to nausea during treatment for mental impairment and may possess α-adrenergic blocking activity. THE MERCK INDEX 10th Ed. 3596 and PHYSICIANS DESK REF., 38th Ed. 1984, pp 911–912. In contrast, certain of the compounds of the formula used in the present invention have antinauseant properties and are not α-adrenergic blocking agents, cholinomimetics, cholinesterase inhibitors or stimulants.

2-Alkoxy-N-(1-azabicyclo[2.2.2]oct-3-yl)benzamides and thiobenzamides and their use in a method for increasing gastric emptying and alleviating emesis, particularly emesis due to administration of platinum and anticancer drugs such as cisplatin are disclosed in co-pending U.S. application Ser. No. 597,275 filed Apr. 6, 1984. Certain of these 2-alkoxy-N-(1-azabicyclo[2.2.2]oct-3-yl)benzamides are also disclosed in Fr. Pat. No. 2.529.548 and European Patent application No. 099.789A and their use as gastrointestinal motility accelerators and as potentiators for medicaments, especially analgesics such as aspirin and paracetamol is also disclosed. Certain of the compounds are also disclosed as useful as analgesics-antipsychotics in Brit. Patent application No. 2,125,398A.

Syntheses of certain N-(1-azabicyclo[2.2.2]oct-3-yl)benzamides have been reported by E. E. Mikhalina, et al., in KHIM-FARM. Zh. (1973) 7 (8) p. 20–24: C.A. 79 146358a. The compounds were reported to possess narcotic, nerve center blocking and hypotensive activity.

The compound 4-amino-N-(1-azabicyclo[2.2.2]oct-3-yl)-3-chloro-5-trifluoromethyl-benzamide has been reported in U.S. Pat. No. 4,093,734 in a class of compounds said to be anxiolytics, anticonvulsants, antiemetics and antiulcerogenics.

Certain of the compounds encompassed by Formula I and useful in the method of the present invention and exemplified by N-(7-octahydroindolizinyl)benzamides and N-(1 and 2-quinolizinyl)benzamides are disclosed by structure, method of synthesis and characterization in U.S. Pat. No. 4,213,983 as being useful in treating gastro-intestinal misfunctions. Still other compounds of Formula I useful in the present invention and exemplified by 4-amino-4-chloro-2-methoxy-N-[4'-α,β-(1'-aza-2'-α-phenyl-6'-α-N-bicyclo[4,3,0]decyl)]benzamide and 4-amino-5-chloro-2-methoxy-N-[7'β-(9'β-methyl-1'-aza-5'α-H-bicyclo[4,3,0]nonyl)]benzamide are disclosed by structure, method of synthesis and characterization in European patent application 0067565A1 as dopamine antagonists for treating impaired gastric motility.

SUMMARY OF THE INVENTION

The arylamidoazabicycloalkanes useful in the method of this invention for improving memory or correcting memory deficiency have the general formula:

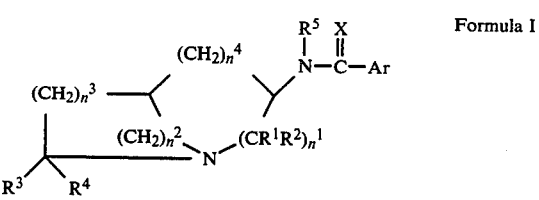

Formula I wherein,
$n^1$, $n^2$, $n_3$ and $n^4$ = 0 to 3
$R^1$, $R^2$, $R^3$, and $R^4$ = H, loweralkyl or phenyl
$R^5$ = H or loweralkyl
X = O or S

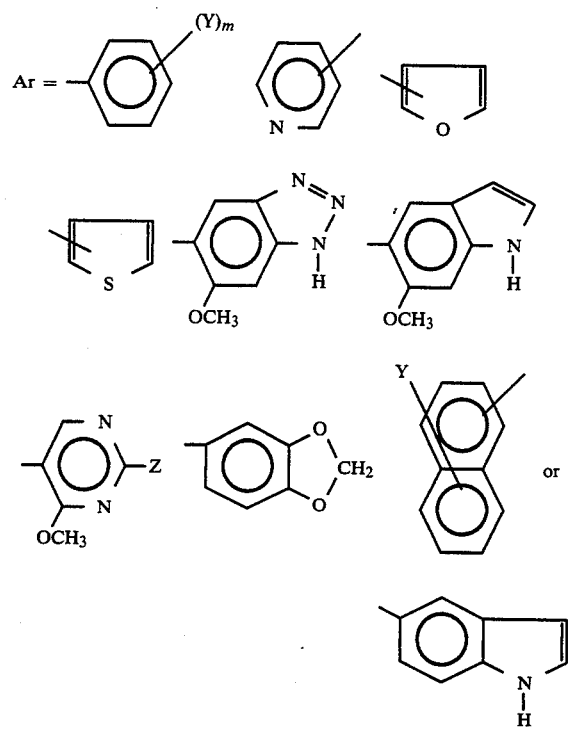

Y = H, loweralkoxy, loweralkylthio, halo, tri fluoromethyl, amino, loweralkylamino, dialkylamino, arylamino, acyl, aminosulfonyl, loweralkylsulfonyl, nitro or aminocarbonyl;
m = 1 to 3
Z = amino, loweralkylamino or diloweralkylamino;
the optical isomers; and the pharmaceutically acceptable acid addition salts, including hydrates and alcoholates thereof.

The compounds are administered using usual pharmaceutical procedures and carriers as described hereinbelow.

In the further definition of symbols and in the formulas hereof and where they appear elsewhere throughout this specification and in the claims, the terms have the following significance.

The term "loweralkyl" as used herein, unless otherwise specified, includes straight ond branched chain radicals of up to eight carbons inclusive and is exemplified by such groups as methyl, ethyl, propyl, isopropyl, butyl, sec-butyl, tert-butyl, amyl, isoamyl, hexyl, heptyl and octyl radicals and the like. The term "loweralkoxy" has the formula —O—loweralkyl.

The term "halo" or "halogen" when referred to herein includes fluorine, chlorine, bromine and iodine unless otherwise stated.

"Pharmaceutically acceptable salts" include acid addition salts and hydrates and alcoholates thereof which are physiologically compatible in living animals. The acid addition salts may be formed by either strong or weak acids. Representative of strong acids are hydrochloric, hydrobromic, sulfuric and phosphoric acids. Representative of weak acids are fumaric, maleic, mandelic, tartaric, citric, oxalic, succinic, hexamic and the like.

The test relied upon to test for memory enhancement involves a passive avoidance procedure with trained mice as described hereinbelow under "Pharmacological Testing."

DETAILED DESCRIPTION OF THE INVENTION

The memory enhancing agents of Formula I above, useful in the method of this invention, may be prepared generally by methods for preparing such amides as described in copending U.S. application Ser. No. 597,275 mentioned above in French Pat. No. 2,529,548, European patent application ED No. 67565 and U.S. Pat. No. 4,213,984. Two principal general methods, A and B, are illustrated in the following equations for preparation of arylamidoazabicycloalkanes:

Method A using an acid chloride

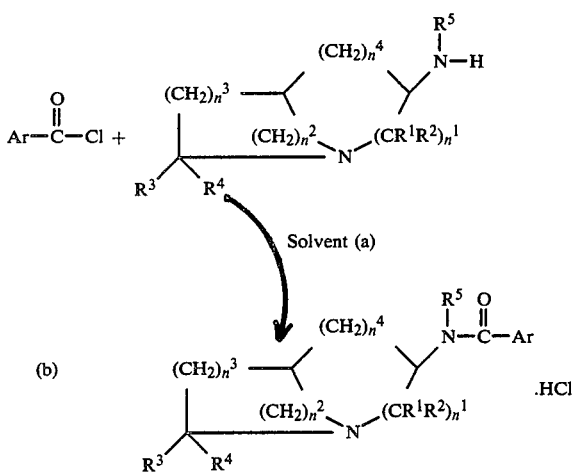

Footnotes:
Symbols are as defined under Formula I, except Ar cannot have unprotected amine substitution.
(a) Suitable solvents are chloroform and diethylether.

Method A is illustrated by Examples 5, 6, 7, and 9.

Method B, using 1,1'-carbonyldiimidazole

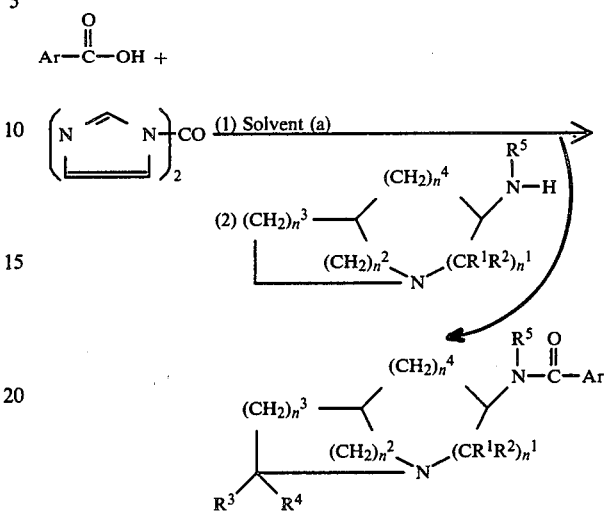

Footnotes:
Symbols are as defined under Formula I.
(a) A suitable solvent is tetrahydrofuran.

Method B is illustrated by Examples 1, 3 and 8.

Compounds of Formula I wherein Ar has a primary amino substituent may also be prepared from a compound prepared by Methods A or B wherein the substituent is nitro by catalytic reduction of the nitro group to the amino group. Alternatively, such amino compounds may be prepared by Method A, utilizing a starting aroyl halide wherein the amino substituent has been protected and thereafter deprotected.

Amide formation may also be accomplished by heating an arylacid ester with the amine in an inert solvent.

The acid addition salts of compounds of Formula I may be prepared in conventional manner by reacting a free base with a pharmaceutically acceptable acid as described above.

The free base of an acid addition salt may be obtained by partitioning the salt in an organic solvent such as methylene chloride and a weak basic aqueous solution and thereafter separating and evaporating the organic solvent layer.

Compounds in this invention may exist in racemic form or they may be separated into optical isomers by procedures described in Fr. Pat. No. 2,529,548. Thus, this invention encompasses racemic and optically active forms.

Preparation of Thioarylamides

The preparation of the thioarylamide compounds encompassed by Formula I may be accomplished by mixing and reacting a benzamide compound of Formula I with a mixture of phosphorus pentasulfide ($P_2S_5$) and potassium sulfide ($K_2S$) or by mixing and reacting 3-aminoquinuclidine with an appropriately substituted arylaldehyde and sulfur. The reaction sequences are illustrated by the following equations:

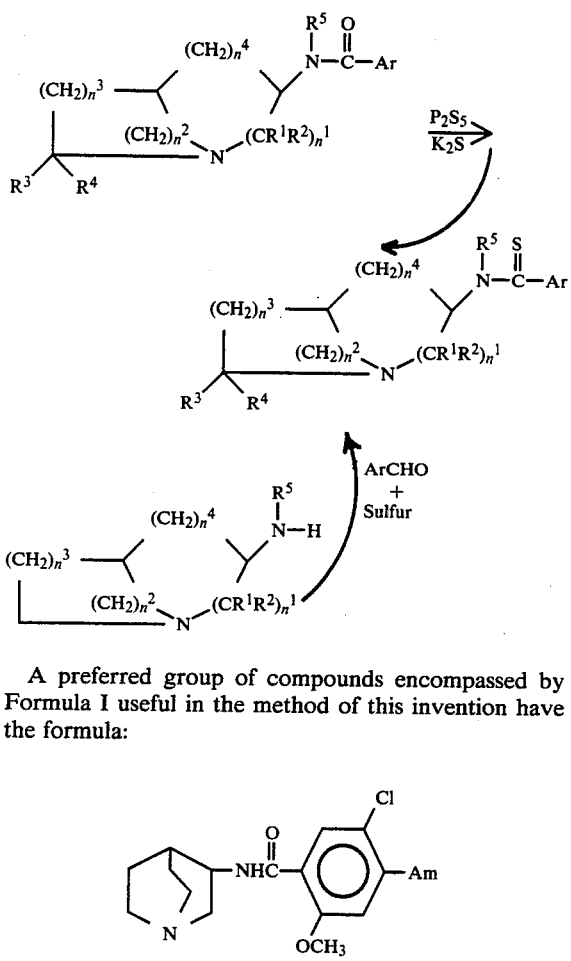

A preferred group of compounds encompassed by Formula I useful in the method of this invention have the formula:

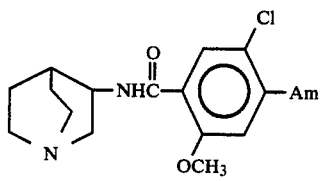

wherein Am is amino (i.e., —NH$_2$) or methylamino.

The following examples are provided merely by way of illustrating the methods of preparation of compounds useful in the method of the invention and are not to be construed as limiting in nature.

EXAMPLE 1

4-Amino-N-(1-azabicyclo[2.2.2]oct-3-yl)-5-chloro-2-methoxybenzamide, fumarate [1:1]

In a closed system equipped with an oil bubbler, 30 ml of tetrahydrofuran was added to a mixture of 4-amino-5-chloro-2-methoxybenzoic acid, 2.02 g, (0.010 mole) and 1,1'-carbonyldiimidazole, 1.62 g (0.010 mole) with stirring. When evolution of carbon dioxide ceased, nitrogen was bubbled through the reaction mixture for 1 hr. A solution of 3-aminoquinuclidine, 1.26 g, (0.010 mole) in 10 ml tetrahydrofuran was added dropwise to the stirred reaction mixture and stirring at room temperature continued for 3 hrs. TLC analysis (3% conc. ammonium hydroxide solution in methanol) showed some product formation. The mixture was heated at reflux temperature for 18 hours and then concentraded to an oil. TLC analysis showed the presence of the product, imidazole, and 3-aminoquinuclidine. The oil was dissolved in methylene chloride (75 ml) and washed twice with 50 ml portions of aqueous sodium bicarbonate solution. The methylene chloride layer was dried over anhydrous magnesium sulfate and concentrated to yield 2.0 g (67%) of a glassy amorphous solid, the free base of the title compound.

In another reaction on a 0.020 mole scale, 5.18 g (83.8%) of the product as the free base was obtained.

The products were combined, dissolved in methanol (20 ml) and the solution and treated with a solution of fumaric acid (2.73 g) in methanol (50 ml). Absolute ether was added to precipitate the salt which was collected by filtration and recrystallized from methanol-water (200:20) with isopropyl ether added to the point of incipient cloudiness. The recrystallized salt (5.38 g) melted at 223°–225° C.

Analysis: Calculated for C$_{19}$H$_{24}$N$_3$O$_6$Cl: C, 53.59; H, 5.68; N, 9.89. Found: C, 53.35; H, 5.72; N, 9.95.

EXAMPLE 2

4-Amino-N-(1-azabicyclo[2.2.2]oct-3-yl)-5-chloro-2-methoxybenzamide, hydrochloride, hydrate (1:1:1)

To an isopropyl alcohol solution of the free base of the title compound such as was obtained by the procedure midway through Example 1 is added in equal molar amount of 37% (conc.) hydrochloric acid. A salt is separated by addition of acetone followed by filtration which is recrystallized from acetone-water to give the title compound, m.p. 158°–160° C.

EXAMPLE 3

N-(1-Azabicyclo[2.2.2]oct-3-yl)-5-chloro-2-methoxy-4-methylaminobenzamide, fumarate [1:1]

To a mixture of 1,1'-carbonyldiimidazole, 1.23 g (0.00756 mole) and 5-chloro-2-methoxy-4-methylaminobenzoic acid, 1.63 g (0.00756 mole) was added 50 ml of tetrahydrofuran. Nitrogen was bubbled into the solution for 30 minutes to remove any carbon dioxide that was present. To the solution was added 3-aminoquinuclidine, 0.95 g, (0.00756 mole) in one portion, and the reaction mixture was stirred at ambient temperature for 16 hours. The reaction mixture was concentrated to an oil which was shown to be 1:1 mixture of the free base of the product and imidazole. The mixture was dissolved in 20 ml methanol and treated with a solution containing 0.47 g fumaric acid in 20 ml of hot methanol. Upon cooling, 1.52 g of white solid formed. Recrystallization from water-methanol gave 0.84 g of the product as a white solid; m.p. 237°–238° C.

Analysis: Calculated for C$_{20}$H$_{26}$N$_3$O$_6$Cl: C, 54.61; H, 5.96; N, 9.55. Found: C, 54.61; H, 5.98; N, 9.51.

EXAMPLE 4

N-(1-Azabicyclo[2.2.2]oct-3-yl)-5-chloro-2-methoxy-4-(methylamino)-benzamide, hydrochloride (1:1)

To an isopropyl alcohol solution of the free base of the title compound, such as was obtained by the procedure of Example 3, is added an equal molar amount of 37% (conc.) hydrochloric acid. The crude salt is separated by filtration and recrystallized from ethanol-water to give the title compound, m.p. 255°–258° C.

EXAMPLE 5

N-(1-Azabicyclo[2.2.2]oct-3-yl)-2-methoxybenzamide, fumarate [1:1]hemihydrate

In a closed system equipped with an oil bubbler, a solution of 2-methoxybenzoyl chloride, 2.76 g (0.0016 mole) in 50 ml absolute ether was added dropwise over 10 min to a stirred solution of 3-aminoquinuclidine, 1.81 g (0.0144 mole) in 100 ml absolute ether. After the addition was completed, the mixture was stirred at room temperature for an additional 2 hrs. The solid hydrochloride salt was collected by filtration under nitrogen. The salt (3.83 g) was dissolved in sodium bicarbonate solution and extracted twice with 25 ml portions of methylene chloride. The extract was dried over magnesium sulfate and concentrated to yield 1.25 g clear oil (33.3%). TLC analysis (3% conc. ammonium hydroxide in methanol) showed the free base to be pure. A solution of 1.17 g of the free base in 5 ml methanol was treated with a solution of 0.52 g fumaric acid in 10 ml methanol. Isopropyl ether was added to give approximately 100 ml of solution from which the fumarate salt precipitated. The salt was collected under nitrogen and dried in a vacuum oven at 60° C. overnight. NMR and elemental analyses showed that the product was a hemihydrate.

Analysis: Calculated for $C_{19}H_{25}N_2O_{6.5}$: C, 59.21; H, 6.54; N, 7.27. Found: C, 59.18; H, 6.30; N, 7.25.

EXAMPLE 6

N-(1-Azabicyclo[2.2.2]oct-3-yl)-2,4-dimethoxybenzamide hydrochloride [1:1]

A mixture of 3-aminoquinuclidine dihydrochloride, 6.95 g, (0.0349), 2,4-dimethoxybenzoyl chloride, 700 g, (0.0349 mole), anhydrous sodium carbonate, 36.99 g, (0.349 mole), 175 ml water, and 175 ml chloroform was stirred rapidly to achieve good mixing of the 2 layers for 20 hrs. The chloroform layer was then separated, washed with water, dried over anhydrous magnesium sulfate, and concentrated to an impure oil. The oil was triturated twice with 20 ml portions of petroleum ether to remove some impurities. The oil was then dissolved in ether and filtered to remove a small amount of insoluble material. The filtrate was treated with ethereal hydrogen chloride and the resulting salt collected to yield 2.70 g (23.7% yield) white solid. The salt was recrystallized from ethanol-isopropyl ether. Further recrystallization from methanol-ethyl ether yielded a white solid, m.p. 211°–212° C. The NMR analysis was satisfactory.

Analysis: Calculated for $C_{16}H_{23}N_2O_3Cl$: C, 58.80; H, 7.09; N, 8.57. Found: C, 58.38; H, 7.13; N, 8.44.

EXAMPLE 7

N-(1-Azabicyclo[2.2.2]oct-3-yl)-2,4-dimethoxybenzamide, sulfate [1:1]

In a closed system equipped with an oil bubbler, a solution of 2,4-dimethoxybenzoyl chloride, 13.08 g, (0.0652 mole) in 200 ml absolute ether was dded dropwise over 30 minutes to a stirred solution of 3-aminoquinuclidine, 7.80 g, (0.0619 mole) in 200 ml absolute ether. The mixture was stirred overnight, and the solid hydrochloride salt of the product was filtered under nitrogen. The material was dried in a vacuum oven at 40° C. to give 18.70 g (92%). A 2.94 g (0.009 mole) portion of the hydrochloride salt in 20 ml methanol was treated with a solution of sodium methoxide prepared from 0.23 g (0.010 mole) sodium metal and 10 ml methanol. After standing a few minutes, the mixture was filtered and the filtrate concentrated on a rotary evaporator, and the residue was triturated with 75 ml methylene chloride. After filtering to remove some insuluble solids, the filtrate was concentrated to yield 2.53 g of the free base of the title compound (97% recovery from the hydrochloride salt). The free base was dissolved in 100 ml acetone and concentrated sulfuric acid (0.483 ml) added dropwise with stirring. The solid that formed was collected under nitrogen to give 2.76 g of the salt which recrystallized from methanol-isopropyl ether and dried in a vacuum oven at 60° C. for 2 hrs and then overnight at 78° C.; m.p. 223°–225° C.

Analysis: Calculated for $C_{16}H_{24}N_2O_7S$: C, 49.47; H, 6.23; N, 7.23. Found: C, 49.41; H, 6.30; N, 7.25.

EXAMPLE 8

N-(1-Azabicyclo[2.2.2]oct-3-yl)-2,4-dimethoxybenzamide, fumarate [1:1.5]

In a closed system equipped with an oil bubbler, tetrahydrofuran, 100 ml, was added to a mixture of 2,4-dimethoxybenzoic acid, 3.64 g (0.020 mole) and 1,1'-carbonyldimidazole, 3.24 g (0.020 mole). No evolution of carbon dioxide was observed and after stirring for 3 hrs, TLC (ethyl acetate) and mass spectral analysis showed that the starting material had reacted to form (2,4-dimethoxybenzoyl) imidazole and imidazole. A solution of 3-aminoquinuclidine, 2.52 g (0.020 mole) in 10 ml tetrahydrofuran was added to the mixture, and the solution was heated to reflux temperature for 1 hr and then allowed to stand overnight at room temperature. A solution of fumaric acid, 2.32 g (0.020 mole in 50 ml methanol was added to the reaction mixture. Tetrahydrofuran was added until the solution became slightly turbid. The solution was chilled in a refrigerator. The solid which precipitated from solution was collected by filtration and found to be a fumarate salt of 3-aminoquinuclidine. The filtrate was concentrated to an oil and triturated with tetrahydrofuran. The solid precipitate which formed on standing was filtered and shown by TLC (3% concentrated ammonium hydroxide in methanol) to be the desired product plus traces of imidazole and 3-aminoquinuclidine. Recrystallization from methanol-iropropyl ether gave 5.41 g white crystalline solid (67% yield calculated as the monofumarate). NMR and elemental analysis showed the salt to contain less than one equivalent of fumaric acid. The salt was dissolved in boiling methanol (50 ml) and treated with an additional 0.77 g (0.0066 mole) fumaric acid in 10 ml hot methanol. Isopropyl ether was added until the hot solution became turbid. The solid obtained on cooling was collected, recrystallized from methanol-isopropyl ether and dried in a vacuum oven at 78° C. overnight. NMR and elemental analysis showed the salt to be a 1.5 fumarate, m.p. 192°–192.5° C.

Analysis: Calculated for $C_{22}H_{28}N_2O_9$: C, 56.89; H, 6.08; N, 6.03. Found: C, 56.81; H, 6.13; N, 6.04.

EXAMPLE 9

N-(1-Azabicyclo[2.2.2]oct-3-yl)-2-propoxybenzamide hydrochloride [1:1]

To a solution of 3.82 g (0.0192 mole) of 3-amino quinuclidine dihydrochloride in about 25 ml of carbon dioxide-free water was added 8 g (0.025 mole) of barium hydroxide octahydrate. The mixture was warmed for 5 minutes and then dried to a powder on a rotary evaporator. While protecting from contamination with carbon dioxide in the atmosphere, the powder was extracted in sequence with hot benzene and a 1:1 mixture of benzene-methylene chloride solution. The combined extracts were dried over magnesium sulfate and the mixture filtered. To the filtrate with agitation was added dropwise a solution of 3.4 g (0.0171 mole) of 2-propoxybenzoyl chloride in 50 ml of methylene chloride. The mixture was warmed on a steam bath to evaporate about 75% of the methylene chloride. Ligroin (60-110) was added and the mixture solidified. The solid was recrystallized from anhydrous ethyl alcohol to give 3.9 g (62.0%), m.p. 210°-211° C.

Analysis: Calculated for $C_{17}H_{25}N_2O_2Cl$: C, 62.86; H, 7.75; N, 8.62. Found: C, 62.62; H, 7.59; N, 8.54.

EXAMPLE 10

N-(1-Azabicyclo[2.2.2]oct-3-yl)-3-methoxy-2-naphthalenecarboxamide, hydrochloride [1:1]

A solution of 1.69 g (0.00768 mole) of 3-methoxy-2-naphthoic acid chloride in 15 ml of methylene chloride was added dropwise to a stirred solution of 0.97 g (0.00768 mole) of 3-aminoquinuclidine in 25 ml of methylene chloride in a closed system equipped with an oil bubbler. The reaction mixture was stirred overnight at ambient temperature, and then concentrated to give an off-white glassy solid. Two recrystallizations from methanol-isopropyl ether gave 1.95 g (73.4%) of the product as an off-white solid which was vacuum dried at ambient temperature, m.p. 248°-252° C.

Analysis: Calculated for $C_{19}H_{23}N_2O_2Cl$: C, 65.79; H, 6.68; N, 8.08. Found: C, 65.40; H, 6.72; N, 8.01.

EXAMPLE 11

4-Amino-N-(1-azabicyclo[2.2.2]oct-3-yl)-5-chloro-2-methoxythiobenzamide fumarate One half mole of 4-amino-N-(1-azabicyclo[2.2.2]oct-3-yl)-5-chloro-2-methoxybenzamide fumarate is partitioned between dilute sodium hydroxide and 400 ml of benzene. The benzene solution is dried with sodium sulfate and distilled to a volume of 250 ml. To this is added a finely-ground mixture of 9 g of phosphorous pentasulfide and 9 g of potassium sulfide. The mixture is refluxed for 4 hr. and an additional 9 g of phosphorous pentasulfide is added and reflux continued for 2 hr. The benzene is decanted off. The solid is dissolved in a suitable solvent and reacted with fumaric acid to give the title compound.

EXAMPLE 12

N-(1-Azabicyclo[2.2.2]oct-3-yl)-4-nitrobenzamide hydrochloride hydrate [1:1:0.75]

A solution of 3-aminoquinuclidine dihydrochloride (5.0 g, 0.0246 mole) in ca. 15 ml methanol/5 ml water was treated with barium hydroxide octahydrate (9.0 g, 0.0286 mole), warmed over steam for ca. 10 min, then taken to dryness on the rotary evaporator at 40°-45° C./35 mm. The resultant dry powder was repeatedly extracted with ca. 6×50 ml dry tetrahydrofuran. The tetrahydrofuran solution was concentrated by boiling until an 80-90 ml volume remained. This clear solution was added dropwise with stirring to a hot solution of 4-nitrobenzoyl chloride (4.36 g., 0.235 mole) in benzene. The solid produced was recrystallized from anhydrous methanol several times to yield 5.13 g of solid, melting at 277°-279° C. Microanalysis and NMR showed 0.75 mole of water present. Mass spec. and IR were satisfactory, yield of title compound was 0.186 mole (79.4%).

Analysis: Calculated for $C_{56}H_{78}Cl_4N_{12}O_{15}$: C, 51.70; H, 6.04; N, 12.92. Found: C, 51.48; H, 5.93; N, 12.91.

EXAMPLE 13

4-Amino-N-(1-azabicyclo[2.2.2]oct-3-yl)benzamide Hydrochloride

A solution of N-(1-azabicyclo[2.2.2]oct-3-yl)-4-nitrobenzamide hydrochloride (11.55 g., 0.037 mole) in 170 ml of 80% aqueous methanol was shaken in a hydrogen atmosphere with a platinum oxide catalyst on the Parr hydrogenator. The calculated volume of hydrogen was taken up in one hour. The catalyst was filtered off through Celite and the filtrate taken to dryness via rotary evaporator. Several recrystallizations of the colorless crystalline residue from 70% aqueous methanol produced a solid melting above 310° C. NMR, MS, and IR supported the proposed structure. Yield of title compound was 8.43 g. (81.2%).

Analysis: Calculated for $C_{14}H_{20}N_3OCl$: C, 59.67; H, 7.15; N, 14.91. Found: C, 59.26; H, 7.11; N, 14.87.

EXAMPLE 14

5-Aminosulfonyl-N-(1-azabicyclo[2.2.2]oct-3-yl)-2-methoxybenzamide Hydrochloride Hydrate [1:1:0.25]

A solution of 3-aminoquinuclidine dihydrochloride (2.5 g, 0.0126 mole) in 25 ml of water was treated with approximately 5 g of KOH and the resultant slurry/solution taken to complete dryness on the rotary evaporator at 50°/35 mm. The dry residue was carefully extracted by repeated triturations with warm tetrahydrofuran until a total volume of 130 ml had been collected and dried over magnesium sulfate. This solution of 3-aminoquinuclidine base was treated with a solution of 2-methoxy-5-sulfamylbenzoyl chloride (2.92 g, 0.0117 mole) in 50 ml of dry tetrahydrofuran by dropwise addition under nitrogen. The resultant very turbid solution was refluxed gently for about 30 min, then freed of tetrahydrofuran by allowing it to evaporate. The residue was taken up in 90% ethanol containing a few drops of ethereal hydrogen chloride, filtered and chilled. The solid produced was then recrystallized again to yield 4.3 g (97%), m.p. 233°-234° C. NMR, MS, and IR were in support of the structure proposed.

Analysis: Calculated for $C_{60}H_{90}Cl_4N_{12}O_{17}S_4$: C, 47.37; H, 5.96; N, 11.05. Found: C, 47.28; H, 5.93; N, 10.87.

EXAMPLE 15

2-Amino-N-(1-azabicyclo[2.2.2]oct-3-yl)benzamide Dihydrochloride

The free base was liberated from 3-aminoquinuclidine dihydrochloride (4.0 gm, 0.020 mole) using barium hydroxide and keeping the process under dry nitrogen. The base thus obtained (0.018 mole) was dissolved in dry tetrahydrofuran, treated with isatoic anhydride (2.04 gm, 0.018 mole) and brought to reflux. The clear, dark brown solution within five minutes became tan-turbid. Reflux was continued for 1 hr, the excess tetrahydrofuran distilled off, and the residue added to boiling ethanol. A small amount of insoluble solid was filtered off. Chilling produced 3.8 g (68%) crystalline amine base, m.p. 241°-243° C. The base was converted to the hydrochloride salt by reacting with ethereal hydrogen chloride and recrystallized from either hot water-isopropanol or methanol-methylethylketone (1:1) to yield a crystalline solid melting 280.5°-283.5° C. NMR, MS, and IR were satisfactory. MW 318.249.

Analysis: Calculated for $Cl_2N_3OC_{14}H_{21}$: C, 52.84; H, 6.65; N, 13.20. Found: C, 52.90; H, 6.54; N, 13.24.

EXAMPLE 16

N-(1-Azabicyclo[2.2.2]oct-3-yl)-2-pyridinecarboxamide Fumarate [1:1]

Tetrahydrofuran (50 ml) was added to a mixture of picolinic acid (2.46 g, 0.020 mole) and 1,1'-carbonyldiimidazole (3.24 g, 0.020 mole) and the mixture stirred in a closed system equipped with an oil bubbler until evolution of carbon dioxide ceased. Nitrogen was then bubbled through the reaction mixture to sweep out any remaining carbon dioxide. 3 Aminoquinuclidine (2.52 g, 0.020 mole) was added to the reaction mixture in one portion and the mixture heated at reflux temperature for 1 hr while continuing to saturate the mixture with nitrogen. After cooling, the mixture was concentrated to a brown oil containing the product, imidazole, and a small amount of 3-aminoquinuclidine. The oil was dissolved in methylene chloride (50 ml) and washed 3 times with 50 ml portions of water. The methylene chloride solution was dried over anhydrous magnesium sulfate and concentrated to an oil. The oil was dissolved in ether and filtered to remove a small quantity of insoluble material. The filtrate was concentrated to give 2.38 g free base (51.4%) which was redissolved in 100 ml ether and treated with a solution of fumaric acid (1.20 g) in 50 ml methanol and the mixture triturated to induce crystallization. The solid salt was collected under nitrogen to yield 3.14 g of white solid. TLC analysis (3% conc. ammonium hydroxide solution in methanol) showed only a trace of impurity.

Mass spectrum (EI)-m/e (% relative intensity): 231 (19), 161 (16), 125 (22), 109 (80), 106 (28), 98 (24), 96 (29), 79 (29), 78 (73), 70 (100), 45 (22), 42 (45), and 41 (20).

Analysis: Calculated for $C_{17}H_{21}N_3O_5$: C, 58.78; H, 6.09; N, 12.10. Found: C, 58.58; H, 6.10; N, 12.04.

EXAMPLE 17

N-(1-Azabicyclo[2.2.2]oct-3-yl)benzamide, Fumarate [1:1]

In a closed system equipped with an oil bubbler, a solution of benzoyl chloride (3.51 g, 0.020 mole) in 100 ml absolute ether was added dropwise over 10 min to a stirred solution of 3-amino-quinuclidine (2.52 g, 0.020 mole) in 100 ml absolute ether. After the addition was completed, the mixture was stirred an additional 1.5 hr, and the solid hydrochloride salt was filtered under nitrogen. The salt was dissolved in methanol and treated with a solution of sodium methoxide prepared from 0.58 g sodium metal (0.025 ml) in 20 ml methanol. The mixture was concentrated and the residual material triturated with methylene chloride (50 ml), filtered, and the filtrate concentrated to give a yellow solid. The solid was triturated with a small amount of acetone and then with 50 ml boiling toluene. The resulting solution was decanted away from some insoluble gummy material. Isooctane was added to the hot toluene solution until the solution was turbid. After standing overnight, the solid free base was collected (2.23 g). The filtrate was concentrated and the residual solid recrystallized from toluene-isooctane to yield an additional 0.35 g of the free base, m.p. 159°–160° C., total yield 2.58 g (56%). The free base was dissolved in 100 ml acetone and treated with a solution of fumaric acid (1.30 g, 0.0112 mole) in 30 ml methanol. The solution was concentrated to give a solid residue which was recrystallized from methanol-isopropyl ether to give 3.03 g of the product, m.p. 187°–190° C. Mass spectrum (E.I.) m/e (% relative intensity) 230 (14), 125 (16), 109 (76), 105 (90), 98 (23), 96 (21), 84 (17), 77 (69), 70 (100), 51 (23), 95 (25), 42 (42).

Analysis: Calculated for $C_{18}H_{22}N_2O_5$: C, 62.42; H, 6.40; N, 8.09. Found: C, 62.01; H, 6.46; N, 7.99.

EXAMPLE 18

N-(1-Azabicyclo[2.2.2]oct-3-yl)-2-furancarboxamide Hydrochloride

In a closed system equipped with an oil bubbler, a solution of 3-amino-quinuclidine (2.52 g, 0.020 mole) in 10 ml anhydrous ether was added dropwise to a stirred solution of furoyl chloride (3.26 g, 0.025 mole) in 100 ml anhydrous ether. After the addition was completed (5 min), the mixture was stirred an additional hour and the solid collected under nitrogen to give 4.73 g (73.7% yield) of the hydrochloride salt. TLC (3% concentrated ammonium hydroxide in methanol) showed a small amount of impurity which was not removed by recrystallization. The salt was dissolved in 20 ml of water, basified with 6N sodium hydroxide solution, and extracted three times with 20 ml portions of methylene chloride. The combined extract was dried over magnesium sulfate and concentrated to yield 2.37 g viscous yellow oil. The oil was dissolved in 20 ml methanol, treated with excess ethereal hydrogen chloride solution and diluted with 100 ml anhydrous ether. The salt crystallized on trituration and was collected under nitrogen to give 1.84 g off-white solid. This solid was recrystallized from methanol-isopropyl ether to give 1.63 g white solid, m.p. 249°–251° C. Mass spectrum (E.I.)-m/e (% relative intensity): 220 (19), 109 (74), 96 (29), 95 (100), 84 (14), 70 (83), 42 (52), 41 (20), 39 (47).

Analysis: Calculated for $C_{12}H_{17}N_2O_2Cl$: C, 56.14; H, 6.67; N, 10.91. Found: C, 56.06; H, 6.69; N, 10.77.

EXAMPLE 19

N-(1-Azabicyclo[2.2.2]oct-3-yl)-2-fluorobenzamide, Monohydrochloride

In a closed system, a solution of 3-aminoquinuclidine (2.52 g, 0.020 mole) in 10 ml anhydrous ether was added dropwise to a stirred solution of 2-fluorobenzoyl chloride (3.13 g, 0.020 mole) in 100 ml anhydrous ether. After the addition was complete, the mixture was stirred another hour and the solid product (as the hydrochloride salt) was collected by filtration under nitrogen to give 4.75 g (84%). TLC analysis (3% conc. ammonium hydroxide in methanol) showed the presence of 3-aminoquinuclidine. The salt was dissolved in 10 ml water, basified with 6N sodium hydroxide solution, and extracted three times with 50 ml portions of methylene chloride. The combined extract was dried over magnesium sulfate and concentrated to give 3.67 g of the product as the free base. Recrystallization from toluenei-sooctane gave 2.33 g of a white solid (some toluene insoluble material was removed by decanting the hot toluene solution). The solid free base was dissolved in 10 ml methanol, treated with excess ethereal hydrogen chloride and 100 ml isopropyl ether was added. The salt separated from solution as an oil, but crystallized on trituration. The white solid was collected under nitrogen to give 2.60 g; m.p. 233°–234° C. Mass spectrum (E.I.) m/e (% relative intensity): 248 (15), 125 (13), 123 (100), 109 (80), 96 (24), 95 (45), 84 (14), 75 (19), 70 (64), 42 (44), 41 (18).

Analysis: Calculated for $C_{14}H_{18}N_2OFCl$: C, 59.05; H, 6.37; N, 9.84. Found: C, 58.78; H, 6.40; N, 9.86.

EXAMPLE 20

N-(1-Azabicyclo[2.2.2]oct-3-yl)-2-thiophenecarboxamide Monohydrochloride

Tetrahydrofuran (30 ml) was added with stirring to a mixture of 2-thiophene carboxylic acid (2.56 g, 0.020 mole) and 1,1'-carbonyldiimidazole (3.24 g, 0.020 mole). When solution of carbon dioxide ceased, nitrogen was bubbled through the solution for 1 hr to free the solution of carbon dioxide. 3-Aminoquinuclidine (2.52 g, 0.020 mole) was added in one portion and the mixture heated to reflux temperature for one hour while continuing to saturate the reaction mixture with nitrogen. After cooling, the mixture was concentrated, the residual oil dissolved in 40 ml methylene chloride, and washed three times with 20 ml portions of water. The methylene chloride solution was dried over magnesium chloride and concentrated to yield 2.57 g (54.4%) gummy white material. The amide was dissolved in a methanol-ether mixture treated with ethereal hydrogen chloride and diluted with ether, causing the salt to separate an oil which crystallized on trituration. The salt was collected under nitrogen (2.22 g) and recyrstallized from methanol-isopropyl ether to give 1.81 g white crystalline solid, m.p. 245°-246° C. Mass spectrum (E.-I.)-m/e (% relative intensity): 236 (17), 125 (19), 111 (100), 109 (65), 96 (23), 84 (18), 83 (24), 82 (17), 70 (84), 42 (45), 41 (20), 39 (43).

Analysis: Calculated for $C_{12}H_{17}N_2OSCl$: C, 52.84; H, 6.28; N, 10.27. Found: C, 52.88; H, 6.34; N, 10.36.

EXAMPLE 21

N-(1-Azabicyclo[2.2.2]oct-3-yl)2,6-dimethoxybenzamide Monohydrochloride

In a closed system equipped with an oil bubbler, a solution of 2,6-dimethoxybenzoyl chloride (1.89 g, 0.0095 mole) in 20 ml diethyl ether was added dropwise to a stirred solution of 3-aminoquinuclidine (1.26 g, 0.010 mole) in 50 ml of diethyl ether. After the addition was completed, the reaction mixture was stirred for 15 min, and the precipitate that had formed was filtered under nitrogen. The wet (hygroscopic) solid was immediately recrystallized from methanol-isopropyl ether to give 1.85 g (60%) of the product. The material was vacuum dried for 4 hr at 98° C., m.p. 266°-268° C.

Analysis: Calculated for $C_{16}H_{23}N_2O_3Cl$: C, 58.80; H, 7.09; N, 8.57. Found: C, 58.44; H, 7.17; N, 8.51.

EXAMPLE 22

N-(1-Azabicyclo[2.2.2]oct-3-yl)-1H-indole-5-carboxamide

Tetrahydrofuran (50 ml) was added to a mixture of indole-5-carboxylic acid (2.42 g, 0.016 mole) and 1,1'-carbonyldiimidazole (2.43 g, 0.015 mole). The mixture was stirred for 1 hr while nitrogen was bubbled through the solution to remove the carbon dioxide that was evolved. Then 3-aminoquinuclidine (1.89 g, 0.015 mole) was added in one portion, and the mixture was stirred for 60 hr at room temperature. The solid product was collected by filtration to yield 3.75 g (86.8%). Recrystallization from methanol-isopropyl ether (with chilling) gave 1.89 g of the product as an off-white solid; m.p. 293°-295° C. The solid was vacuum dried at 82° C. for 16 hr, m.p. 293°-295° C.

Analysis: Calculated for $C_{16}H_{19}N_3O$: C, 71.35; H, 7.11; N, 15.60. Found: C, 70.96; H, 7.15; N, 15.38.

EXAMPLE 23

N-(1-Azabicyclo[2.2.2]oct-3-yl)-2-methoxy-5-(methylsulfonyl)-benzamide, Monohydrochloride A solution of 3-aminoquinuclidine (1.50 g, 0.0119 mole) in 20 ml of tetrahydrofuran was added dropwise to a stirred solution of 2-methoxy-5-methanesulfonylbenzoyl chloride (2.95 g, 0.0119 mole) in 100 ml tetrahydrofuran. The mixture was stirred at ambient temperature for 20 hr and filtered to yield 4.00 g (89.7%) of the product as the hydrochloride salt. The material was heated in 100 ml of boiling absolute ethanol and 50 ml methanol was added to give a clear solution. The solution was evaporated to a volume of 100 ml and cooled. The precipitate which formed was collected by filtration and vacuum dried at 110° C. for 8 hr; m.p. 219°-221° C.

Analysis: Calculated for $C_{16}H_{23}N_2O_4SCl$: C, 51.26; H, 6.18; N, 7.47. Found: C, 51.19; H, 6.6; N, 7.35.

EXAMPLE 24

N-(1-Azabicyclo[2.2.2]oct-3-yl)-5-bromo-2,4-dimethoxybenzamide Monohydrochloride A solution of 3-aminoquinuclidine (1.12 g, 0.0089 mole) in 20 ml tetrahydrofuran was added dropwise to a stirred solution of 5-bromo-2,4-dimethoxybenzoyl chloride (2.50 g, 0.0089 mole) in 100 ml tetrahydrofuran. The mixture was stirred at ambient temperature for 65 hr, and the solid was collected by filtration to yield 2.77 g. Recrystallization from methanol-isopropyl ether gave 1.45 g (40.2%), m.p. 240°-243° C.

Analysis: Calculated for $C_{16}H_{21}N_2O_3Br$: C, 47.37; H, 5.47; N, 6.90. Found: C, 47.23; H, 5.62; N, 6.85.

EXAMPLE 25

N-(1-Azabicyclo[2.2.2]oct-3-yl)-3-methoxybenzamide, Monohydrochloride

In a closed system, a solution of 3-methoxybenzoyl chloride (7.18 g, 0.04206 mole) in 30 ml ether was added dropwise to a stirred solution of 3-aminoquinuclidine (5.30 g, 0.04206 mole) in 100 ml of ether. The reaction mixture was stirred at ambient temperature for 16 hr. The solid hydrochloride salt was collected under nitrogen and dried in vacuo at ambient temperature to give 11.12 g (87.1%) of the product. The material was recyrstallized from absolute ethanol-isopropyl ether to give 7.69 g. The product was vacuum dried for 20 hr over refluxing ethanol, and then for 24 hr over refluxing isooctane; m.p. 214°-215° C.

Analysis: Calculated for $C_{15}H_{21}N_2O_2Cl$: C, 60.70; H, 7.13; N, 9.44. Found: C, 60.45; H, 7.15; N, 9.40.

EXAMPLE 26

N-(1-Azabicyclo[2.2.2]oct-3-yl)-3-fluorobenzamide, Monohydrochloride

In a closed system, a solution of 3-fluorobenzyl chloride (7.93 g, 0.050 mole) in 30 ml ether was added dropwise to a stirred solution of 3-aminoquinuclidine (6.3 g, 0.050 mole) in 100 ml ether. After the addition was completed, the mixture was stirred at ambient temperature for 16 hr. The solid hydrochloride salt was collected under a nitrogen atmosphere and vacuum dried for 2 hr, to yield 13.11 g (92.1%). The salt was recrystallized from absolute ethanol-isopropyl ether to give 8.87 g of a white solid. The material was recrystallized from ethanol, and vacuum dried for 12 hr at 70° C., m.p. 257°-258° C.

Analysis: Calculated for $C_{14}H_{18}N_2OFCl$: C, 59.05; H, 6.37; N, 9.84. Found: C, 59.05; H, 6.41; N, 9.80.

The preparations of certain compounds encompassed by Formula I and useful in the present invention listed in the following Example 27 a to n are demonstrated and illustrated by structure in U.S. Pat. No. 4,213,983.

EXAMPLE 27 (A)–(N)

(a) 4-Acetylamino-4-chloro-2-methoxy-N-(2-quinolizidinyl)benzamide. (Compound identified in Ex. 1 of U.S. Pat. No. 4,213,983).

(b) 4-Amino-5-chloro-2-methoxy-N-(2-quinolizidinyl)benzamide (Compound identified in Ex. 2 of U.S. Pat. No. 4,213,983).

(c) 4-Acetylamino-5-chloro-2-methoxy-N-(7-octahydroindolizidinyl)benzamide. (Compound identified in Ex. 3 of U.S. Pat. No. 4,213,983).

(d) 4-Amino-5-chloro-2-methoxy-N-(7-octahydroindolizidinyl)benzamide. (Compound identified in Ex. 4 of U.S. Pat. 4,213,983).

(e) 4-Acetylamino-5-chloro-2-methoxy-N-(3-quinolizidinyl)benzamide. (Compound identified in Ex. 5 of U.S. Pat. No. 4,213,983).

(f) 4-Amino-5-chloro-2-methoxy-N-(3-quinolizidinyl)benzamide. (Compound identified in Ex. 6 of U.S. Pat. No. 4,213,983).

(g) 4-Acetylamino-5-chloro-2-methoxy-N-(1-quinolizidinyl)benzamide. (Compound identified in Ex. 7 of U.S. Pat. No. 4,213,983).

(h) 4-Amino-5-chloro-2-methoxy-N-(1-quinolizidinyl)benzamide. (Compound identified in Ex. 8 of U.S. Pat. No. 4,213,983).

(i) 4-Acetylamino-5-chloro-2-methoxy-N-(2-pyrido[1,2-a]pyrazinyl)benzamide. (Compound identified in Ex. 11 of U.S. Pat. No. 4,213,983).

(j) 4-Acetylamino-5-chloro-2-methoxy-N-(2-octahydroindolizinyl)benzamide. (Compound identified in Ex. 13 of U.S. Pat. No. 4,213,983).

(k) 4-Amino-5-chloro-2-methoxy-N-(2-octahydroindolizinyl)benzamide. (Compound identified in Ex. 14 of U.S. Pat. No. 4,213,983).

(l)4-Acetylamino-4-chloro-2-methoxy-N-(6-methyl-2-quinolizidinyl)benzamide. (Compound identified in Ex. 15 of U.S. Pat. No. 4,213,983).

(m) 4-Amino-5-chloro-2-methoxy-N-(6-methyl-2-quinolizidinyl)benzamide. (Compound identified in Ex. 16 of U.S. Pat. No. 4,213,983). and, (n) 4-Amino-5-chloro-2-methoxy-N-(6-methyl-2-quinolizidinyl)benzamide. (Compound identified in Ex. 17 of U.S. Pat. No. 4,213,983).

The preparation of certain compounds encompassed by Formula I and useful in the present invention listed in the following Example 28 a to z and Example 29 a and b are demonstrated and illustrated by structure in European patent application publication No. 0067565A1 as follows:

EXAMPLE 28 (A)–(Z)

(a) 4-Amino-5-chloro-2-methoxy-N-[4'α,β-(1'-aza-2'-α-phenyl-6'-α-H-bicyclo[4,3,0]decyl)]benzamide (compound isentified in Example 5 of European Pat. No. 0067565).

(b) 4-Acetamido-5-chloro-2-methoxy-N-[7'β-(9'β-methyl-1'-aza-5α-H-bicyclo[4,3,0]nonyl)]benzamide (compound identified in Example 6 of European Pat. No. 0067565).

(c) 4-Acetamido-5-chloro-2-methoxy-N-[7'α-(9'β-methyl-1'-aza-5'α-bicyclo[4,3,0]nonyl)]benzamide (compound identified in Example 7 of European Pat. No. 0067565).

(d) 4-Amino-5-chloro-2-methoxy-N-[7'β-(9'β-methyl-1'-aza-5'α-H-bicyclo[4,3,0]nonyl)]benzamide (compound identified in Example 8 of European Pat. No. 0067565).

(e) 4-Amino-5-chloro-2-methoxy-N-[7'α-(9'β-methyl-1'-aza-5'-α-H-bicyclo[4,3,0]nonyl)]benzamide (compound identified in Example 9 of European Pat. No. 0067565).

(f) 4-Acetamido-5-chloro-2-methoxy-N-[7'β-(9''-methyl-1'-aza-5'α-H-bicyclo[4,3,0]nonyl)]benzamide (compound identified in Example 10 of European Pat. No. 0067565).

(g) 4-Amino-5-chloro-2-methoxy-N-[7'β-(9'α-methyl-1'-aza-5α-H-bicyclo[4,3,0]nonyl)]benzamide (compound identified in Example 11 of European No. 0067565).

(h) 4-Acetamido-5-chloro-2-methoxy-N-[7'α-(9'-α-methyl-1'-aza-5'α-H-bicyclo[4,3,0]nonyl)]benzamide (compound identified in Example 12 of European No. 0067565).

(i) 4-Amino-5-chloro-2-methoxy-N-[n'α-(7'-α-(9'-α-methyl-1'-aza-5α-H-bicyclo[4,3,0]nonyl)]benzamide (compound identified in Example 13 of European No. 0067565).

(j) 4-Acetamido-5-chloro-2-methoxy-N-[7'β-(9',9'dimethyl)-1'-aza-5'αH-bicyclo[4,3,0]nonyl)]benzamide (compound identified in Example 14 of European No. 0067565).

(k) 4-Amino-5-chloro-2-methoxy-N-(7'β-(9,9'-dimethyl)-1'-aza-5'α-H-bicyclo[4,3,0]nonyl)]benzamide (compound identified in Example 15 of European No. 0067565).

(l) 4-Acetamido-5-chloro-2-methoxy-N-[7'α-(9',9'-dimethyl-1'-aza-5'-α-H-bicyclo[4,3,0]nonyl)]benzamide (compound identified in Example 16 of European No. 0067565).

(m) 4-Amino-5-chloro-2-methoxy-N-[7'α-(9',9'-dimethyl)-1'-aza-5'α-H-bicyclo[4,3,0]nonyl)]benzamide (compound identified in Example 17 of European No. 0067565).

(n) 4-Acetamido-5-chloro-2-methoxy-N-[7'β(9'-methyl-3'-phenyl-1'-aza-5'α-H-bicyclo[4,3,0]nonyl)]benzamide, Isomer I (compound identified in Example 18 of European No. 0067565).

(o) 4-Amino-5-chloro-2-methoxy-N-[7'β-(9'-methyl 3'-phenyl-1'-aza-5'α-H-bicyclo[4,3,0]nonyl)]benzamide monohydrochloride, Isomer I (compound identified in Example 19 of European No. 0067565).

(p) 4-Acetamido-5-chloro-2-methoxy-N-[7'β-(9'-methyl-3'-phenyl-1'-aza-5'α-H-bicyclo[4,3,0]nonyl]benzamide, Isomer 2 (compound identified in Example 20 of European No. 0067565).

(q) 4-Amino-5-chloro-2-methoxy-N-[7'β-(9'methyl-3'-phenyl-1'-aza-5'α-H-bicyclo[4,3,0]nonyl)]benzamide, Isomer 2 (compound identified in Example 21 of European No. 0067565).

(r) 4-Acetamido-5-chloro-2-methoxy-N-[7'β-(9'-methyl-3'-phenyl-1'-aza-5'α-H-bicyclo[4,3,0]nonyl)-]benzamide, Isomer 3 (compound identified in Example 22 of European No. 0067565).

(s) 4-Amino-5-chloro-2-methoxy-N-[7'β-(9'-methyl 3'-phenyl-1'-aza-5'α-H-bicyclo[4,3,0]nonyl]benzamide, Isomer 3 (compound identified in Example 23 of European No. 0067565).

(t) 4-Amino-5-chloro-2-methoxy-N-[4′β-(7′β-methyl-1′-aza-6′α-H-bicyclo[4,4,0]decyl)]benzamide (compound identified in Example 25 of European No. 0067565).

(u) 4-Acetamido-5-chloro-2-methoxy-N-[4′α-(7′β-methyl-1′aza-6′α-H-bicyclo[4,4,0]decyl)]benzamide with 10% 4′β isomer (mixture identified in Example 26 of European No. 0067565).

(v) 4-Amino-5-chloro-2-methoxy-N-[4′α-(7′β-methyl-1′-aza-6′α-H-bicyclo[4,4,0]decyl)]benzamide with 10% 4′β-isomer (mixture identified in Example 27 of European No. 0067565).

(w) 4-Acetamido-5-chloro-2-methoxy-N-[4′β-(7′β-(7′α-methyl-1′-aza-6′α-H-bicyclo[4,4,0]decyl)]benzamide (compound identified in Example 28 of European No. 0067565).

(x) 4-Amino-5-chloro-2-methoxy-N-[4′β-(7′α-methyl-1′-aza-6′α-H-bicyclo[4,4,0]decyl]benzamide (compound identified in Example 29 of European No. 0067565).

(y) 4-Acetamido-5-chloro-2-methoxy-N-[7′β-(5′α-methyl-1′-aza-bicyclo[4,3,0]nonyl)]benzamide (compound identified in Example 30 of European No. 0067565).

(z) 4-Acetamido-5-chloro-2-methoxy-N-[7′β-(9′α-ethyl-1′-aza-5′-H-bicyclo[4,3,0]nonyl)]benzamide (compound identified in Example 32 of European No. 0067565).

EXAMPLE 29(a)–(b)

(a) 4-Amino-5-chloro-2-methoxy-N-[7′β-(9′α-ethyl-1′-aza-5′α-H-bicyclo[4,3,0]nonyl)]benzamide (compound identified in Example 33 of European No. 0067565).

(b) 4-Acetamido-5-chloro-2-methoxy-N-[7′β-(9′α-isopropyl-1′-aza-5′α-H-bicyclo[4,3,0]nonyl)]benzamide (compound identified in Example 34 of European No. 0067565).

EXAMPLE 30

N-(1-Azabicyclo[2.2.2]oct-3-yl)-6-methoxy-1H-benzotriazole-5-carboxamide

Following the procedure of Example 22, 6-methoxy-1H-benzotriazole-5-carboxylic acid, 1,1′-carbonyldiimidazole and 3-aminoquinuclidine are reacted to give the title compound.

EXAMPLE 31

N-(1-Azabicyclo[2.2.2]oct-3-yl)-6-methoxy-1H-indole-5-carboxamide

Following the procedure of Example 22, indole-6-methoxy-5-carboxylic acid, 1,1′-carbonyldiimidazole and 3-aminoquinuclidine are reacted to give the title compound.

EXAMPLE 32

N-(1-Azabicyclo[2.2.2]oct-3-yl)-2-(dimethylamino)-4-methoxy-5-pyrimidinecarboxamide Following the procedure of Example 22, 2-(dimethylamino)-4-methoxy-5-pyrimidinecarboxylic acid, 1,1′-carbonyldiimidazole and 3-aminoquinuclidine are reacted to give the title compound.

EXAMPLE 33

N-(1-Azabicyclo[2.2.2]oct-3-yl)-4-methoxy-2-(methylamino)-5-pyrimidinecarboxamide Following the procedure of Example 22, 4-methoxy-2-(methylamino)-5-pyrimidinecarboxylic acid, 1,1′-carbonyldiimidazole and 3-aminoquinuclidine are reacted to give the title compound.

EXAMPLE 34

2-Amino-N-(1-azabicyclo[2.2.2]oct-3-yl)-4-methoxy-5-pyrimidinecarboxamide

Following the procedure of Example 22, 2-amino-4-methoxy-5-pyrimidinecarboxylic acid, 1,1′-carbonyldiimidazole and 3-aminoquinuclidine are reacted to give the title compound.

EXAMPLE 35

N-(1-Azabicyclo[2.2.2]oct-3-yl)-1,3-benzodioxole-5-carboxamide

Following the procedure of Example 22, 1,3-benzodioxole-5-carboxylic acid, 1,1′-carbonyldiimidazole and 3-aminoquinuclidine are reacted to give the title compound.

Pharmacological Testing (Mice)

The test relied upon to indicate effectiveness of the compounds in the method of this invention as follows involves a passive avoidance procedure which is the type of procedure most often used to evaluate compounds for their effect on memory and learning.

There are three phases to the behavioral procedure: adaptation, training and testing. Following 24 hrs of water deprivation, the mice are given an adaptation session during which they are allowed to freely explore the chamber and learn the location of the drinking spout. The session is terminated when the animals have completed 5 seconds of drinking. The mice are then given free access to water for 1.5 hrs in their home cages. During the training session, 24 hrs later, the mice are permitted 5 seconds access to the drinking tube after which time the shock circuit is automatically activated and all subsequent contracts with the tube are punished. The training session is terminated when the mice either fail to touch the tube for a 60 seconds period or receive the maximum number of shocks (5). The latency to complete the initial 5 seconds of drinking, as well as the number of shocks each animal receives is recorded. The animals are then returned to their home cages and given free access to water for the next 24 hrs.

Retention is tested 48 hrs later by once again placing the mice into the lick-suppression chamber and recording the time it takes each animal to complete the 5 seconds of drinking from the water spout. Mice failing to complete the 5 seconds of drinking within 2000 seconds are removed from the apparatus and assigned a maximum test latency score of 2000. Test compound or saline are given 30 minutes prior to the retention task.

As indicated in Table 1, the compound of Example 2; namely, 4-amino-N-(1-azabicyclo[2.2.2]oct-3-yl)-5-chloro-2-methoxybenzamide hydrochloride hydrate[1:1:1], significantly increases the time required to complete the drinking task. This increased latency is a measure of memory improvement in the trained animals.

It should be noted that the increased latency is not due to a general debilitation of the animals since untrained animals treated with the same doses of the compound of Example 2 do not show a similar delayed latency to drinking.

TABLE 1

| | Effects on Memory in Mice | | |
|---|---|---|---|
| Compound | Dose (mg/kg, i.p.) | Latency to Complete 5 sec. of Drinking ($\bar{X} \pm SE$) | pH |
| Saline | 0 | 413 ± 69 | — |
| Example 2 | 56 | 511 ± 193 | ns |
| Example 2 | 75 | 354 ± 88 | ns |
| Example 2 | 100 | 1182 ± 222 | p 0.02 |
| Example 2 | 130 | 1347 ± 160 | p 0.002 |

Pharmaceutical Compositions

The pharmaceutical compositions used in the method of this invention for administration to animals and humans are comprised of, as active ingredients, at least one of the compounds of Formula I, according to the invention, in association with a pharmaceutical carrier or excipient. The compounds are thus presented in a therapeutic composition for oral, parenteral, subcutaneous, intramuscular, intraperitoneal, intravenous, or rectal administration. Thus, for example, compositions for oral administration can take the form of elixirs, capsules, tablets, or coated tablets containing carriers conveniently used in the pharmaceutical art. Suitable tableting excipients include lactose, potato and maize starches, talc, gelatin, stearic and silicic acids, magnesium stearate and polyvinyl pyrrolidones.

For parenteral administration, the carrier or excipient can be comprised of a sterile parenterally acceptable liquid; e.g., water or arachis oil contained in ampoules.

In compositions for rectal administration, the carrier can be comprised of a suppository base; e.g., cocoa butter or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be consistent with the dosage form employed in single or multiple unit doses. The exact individual dosages, as well as daily dosages, will of course be determined according to standard medical principles under the direction of a physician or veterinarian. Generally, the pharmacology tests on mice suggest an effective dose for a small animal will be in the range of about 75–130 mg/kg of body weight for a compound such as that of Example 2. Generally, for humans, in the absence of actual testing the amount projected to be required appears to be about 10–100 mg/kg of body weight to produce memory enhancement in humans; for example, in impaired memory of the elderly.

Based on the foregoing projection for effective dosages for humans, daily dosages of about 2 to 4 times the effective dose appear to be reasonable for a total daily dosage range of 20–400 mg/kg of body weight. Obviously, the effective dosage amount may be administered by a variety of unit dosage sizes. The scope of the invention in relation to human dosage is not to be limited by the foregoing projections due to uncertainty in transposing from animal data to human dosages.

What is claimed is:

1. A method for enhancing learning or memory in living animals in need thereof which comprises administering thereto an effective amount for enhancing learning or memory in said animal of a compound selected from the group having the formula:

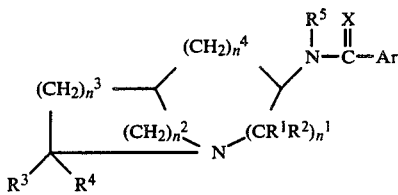

wherein $n^1$, $n^2$, $n^3$, and $n^4$ are zero to three inclusive; $R^1$, $R^2$, $R^3$, and $R^4$ are hydrogen, loweralkyl or phenyl; $R^5$ is hydrogen or loweralkyl; X is oxygen or sulfur; Ar is selected from

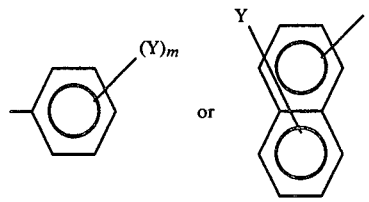

Y is hydrogen, loweralkoxy, loweralkylthio, halo, trifluoromethyl, amino, loweralkylamino, diloweralkylamino, arylamino, acyl, aminosulfonyl, nitro, or aminocarbonyl; m is one to three inclusive; and a pharmaceutically acceptable acid addition salt and a hydrate and an alcoholate thereof and an optical isomer thereof.

2. The method of claim 1 wherein the compound used is 4-amino-N-(azabicyclo[2.2.2]oct-3-yl)-5-chloro-2-methoxybenzamide or a pharmaceutically acceptable acid addition salt thereof.

3. The method of claim 1 wherein the compound used is N-(1-azabicyclo[2.2.2]oct-3-yl)-5-chloro-2-methoxy-4-methylaminobenzamide or a pharmaceutically acceptable acid addition salt thereof.

4. The method of claim 1 wherein the compound used is N-(1-azabicyclo[2.2.2]oct-3-yl)-2-methoxybenzamide or a pharmaceutically acceptable acid addition salt thereof.

5. The method of claim 1 wherein the compound used is N-(1-azabicyclo[2.2.2]oct-3-yl)-2,4-dimethoxybenzamide or a pharmaceutically acceptable acid addition salt thereof.

6. The method of claim 1 wherein the compound used is N-(1-azabicyclo[2.2.2]oct-3-yl)-2-propoxybenzamide or a pharmaceutically acceptable acid addition salt thereof.

7. The method of claim 1 wherein the compound used is N-(1-azabicyclo[2.2.2]oct-3-yl)-3-methoxy-2-naphthalenecarboxamide or a pharmaceutically acceptable acid addition salt thereof.

8. The method of claim 1 wherein the compound used is 4-amino-N-(1-azabicyclo[2.2.2]oct-3-yl)-5-chloro-2-methoxythiobenzamide or a pharmaceutically acceptable acid addition salt thereof.

9. The method of claim 1 wherein the compound used is N-(1-azabicyclo[2.2.2]oct-3-yl)-4-nitrobenzamide or a pharmaceutically acceptable acid addition salt thereof.

10. The method of claim 1 wherein the compound used is 4-amino-N-(1-azabicyclo[2.2.2]oct-3-yl)benzamide or a pharmaceutically acceptable acid addition salt thereof.

11. The method of claim 1 wherein the compound used is 5-aminosulfonyl-N-(1-azabicyclo[2.2.2]oct-3-yl)-2-methoxybenzamide or a pharmaceutically acceptable acid addition salt thereof.

12. The method of claim 1 wherein the compound used is 2-amino-N-(1-azabicyclo[2.2.2]oct-3-yl)benzamide or a pharmaceutically acceptable acid addition salt thereof.

13. The method of claim 1 wherein the compound used is N-(1-azabicyclo[2.2.2]oct-3-yl)benzamide or a pharmaceutically acceptable acid addition salt thereof.

14. The method of claim 1 wherein the compound used is N-(1-azabicyclo[2.2.2]oct-3-yl)-2-fluorobenzamide or a pharmaceutically acceptable acid addition salt thereof.

15. The method of claim 1 wherein the compound used is N-(1-azabicyclo[2.2.2]oct-3-yl)-2,6-dimethoxybenzamide or a pharmaceutically acceptable acid addition salt thereof.

16. The method of claim 1 wherein the compound used is N-(1-azabicyclo[2.2.2]oct-3-yl)-2-methoxy-5-(methylsulfonyl)benzamide or a pharmaceutically acceptable acid addition salt thereof.

17. The method of claim 1 wherein the compound used is N-(1-azabicyclo[2.2.2]oct-3-yl)-5-bromo-2,4-dimethoxybenzamide or a pharmaceutically acceptable acid addition salt thereof.

18. The method of claim 1 wherein the compound used is N-(1-azabicyclo[2.2.2]oct-3-yl)-3-methoxybenzamide or a pharmaceutically acceptable acid addition salt thereof.

19. The method of claim 1 wherein the compound used is N-(1-azabicyclo[2.2.2]oct-3-yl)-3-fluorobenzamide or a pharmaceutically acceptable acid addition salt thereof.

* * * * *